United States Patent
Juneau et al.

(10) Patent No.: US 6,694,796 B2
(45) Date of Patent: Feb. 24, 2004

(54) DEVICE AND METHOD FOR INTRODUCING A KNOWN DUST CONCENTRATION SPIKE FOR CALIBRATING PARTICULATE MATTER CONTINUOUS EMISSION MONITORING SYSTEMS

(75) Inventors: Phillip J. Juneau, Raleigh, NC (US); Robert Baxter, Raleigh, NC (US)

(73) Assignee: B3 Systems, Inc., Raleigh, NC (US)

( * ) Notice: Subject to any disclaimer, the term of this patent is extended or adjusted under 35 U.S.C. 154(b) by 411 days.

(21) Appl. No.: 09/767,386

(22) Filed: Jan. 23, 2001

(65) Prior Publication Data

US 2003/0029221 A1 Feb. 13, 2003

(51) Int. Cl.$^7$ ................................................. G01N 31/00
(52) U.S. Cl. ...................... 73/1.03; 73/1.08; 73/863.23; 73/863.81; 73/863.11
(58) Field of Search ................................ 73/1.06, 1.08, 73/863.23, 863.81, 863.11

(56) References Cited

U.S. PATENT DOCUMENTS

| | | |
|---|---|---|
| 4,197,013 A | 4/1980 | Van Ackeren et al. |
| 4,684,063 A | 8/1987 | Goudy, Jr. |
| 5,312,598 A | 5/1994 | Kersey et al. |
| 5,502,998 A | 4/1996 | Miller et al. |
| 5,544,951 A * | 8/1996 | Alack ...................... 366/163.2 |
| 6,190,461 B1 * | 2/2001 | Alack .......................... 127/22 |

* cited by examiner

Primary Examiner—Hezron Williams
Assistant Examiner—Andre' K. Jackson
(74) Attorney, Agent, or Firm—Myers Bigel Sibley & Sajovec

(57) ABSTRACT

An apparatus for calibrating a particulate matter continuous emission monitoring system includes: a feed unit that supplies particulate matter of a known mass flow rate; an eductor unit connected with the feed unit that receives particulate matter therefrom; a fluidizing unit connected to the eductor that supplies gas to the eductor unit, wherein the particulate matter and gas are combined into a fluidized mixture; and a probe connected to the eductor configured to extend within an industrial stack and deliver the fluidized mixture therein. Such an apparatus can provide accurate data regarding particulate matter concentration that can be compared with readings on the PM CEMS and enable a calibration curve to be generated. A tracer gas injection unit and analyzer may also be included.

29 Claims, 4 Drawing Sheets

DEVICE AND METHOD FOR INTRODUCING A KNOWN DUST CONCENTRATION SPIKE FOR CALIBRATING PARTICULATE MATTER CONTINUOUS EMISSION MONITORING SYSTEMS

FIELD OF THE INVENTION

The present invention relates generally to environmental sampling, and more specifically to the calibration of sampling equipment.

BACKGROUND OF THE INVENTION

Sampling and monitoring the waste stream of industrial apparatus is often required by governmental regulations. Whether the waste stream be liquid, gas, or gas with particulate matter, there are many systems employed to carry out such sampling, which can assist the owner/user of the apparatus being monitored to maintain proper (i.e., legal) levels of specific components of the stream, thereby avoiding violations and accompanying sanctions. Given their role in the industrial process, it is important that the monitoring equipment provide accurate readings for the components it measures.

One system for monitoring gas streams with particulate matter is known as a particulate matter continuous emission monitoring system (PM CEMS). A typical PM CEMS includes an optical or other device that produces a signal that is roughly proportional to the mass concentration of particulate matter in the gas stream. Depending on the regulatory application, the PM CEMS may also use a separate flow monitor to allow calculation of particulate emissions in units of mass per unit time (e.g. pounds per hour). In most cases the relationship between PM CEMS output readings and actual mass emissions is site-specific and must be determined experimentally.

Like any sampling system, it is important for a PM CEMS to be accurate in its monitoring of flue gases. As such, an apparatus for calibrating a PM CEMS would be desirable. It would be particularly desirable to have a calibration method that can be carried out without interruption of operation of the industrial apparatus.

SUMMARY OF THE INVENTION

The present invention can address these needs by providing an apparatus and method for calibrating a particulate matter continuous emission monitoring system. The apparatus comprises: a feed unit that supplies particulate matter of a known concentration; an eductor unit connected with the feed unit that receives particulate matter therefrom; a fluidizing unit connected to the eductor that supplies gas to the eductor unit, wherein the particulate matter and gas are combined into a fluidized mixture; and a probe connected to the eductor configured to extend within an industrial stack and deliver the fluidized mixture therein. Such an apparatus can provide accurate data regarding particulate matter concentration that can be compared with readings on the PM CEMS and enable a calibration curve to be generated.

In one embodiment, the apparatus includes a tracer gas injection unit connected with the probe. The tracer gas injection unit is configured to inject an easily detectable and non-reactive tracer gas into the probe to combine with said fluidized mixture. The concentration of tracer gas in the stack, which can be detected with a tracer gas analyzer, can be used to calculate the concentration of particulate matter in the stack, which in turn can be compared to the PM CEMS reading.

The present invention also encompasses a method of calibrating a particulate matter continuous emission monitoring system. The method comprises the steps of:

(a) providing particulate matter of a known composition and mass flow rate;
(b) fluidizing and heating the particulate matter with a gas;
(c) injecting the fluidized particulate matter into an industrial stack;
(d) recording the PM CEMS instrument response in units of concentration and/or mass flow rate;
(e) separately determining the emissions of particulate matter in the stack from the known injection rate;
(f) repeating steps (a)–(e) for differing concentrations of particulate matter; and
(g) comparing the PM CEMS instrument response with the calculated particulate emissions to generate a calibration curve for the PM CEMS.

This method may also include the injection of tracer gas into the fluidized mixture, wherein step (e) above comprises the measuring the concentration of tracer gas in the stack as an indicator of particulate matter concentration.

Objects of the present invention will be appreciated by those of ordinary skill in the art from a reading of the figures and the detailed description of the preferred embodiments which follow, such description being merely illustrative of the present invention.

BRIEF DESCRIPTION OF THE FIGURES

The accompanying drawings, which are incorporated in and constitute a part of the specification, illustrate embodiments of the invention and, together with the description, serve to explain principles of the invention.

DETAILED DESCRIPTION OF THE INVENTION

The present invention will now be described more particularly hereinafter with reference to the accompanying drawings, in which embodiments of the invention are shown. The invention, however, be embodied in many different forms and is not limited to the embodiments set forth herein; rather, these embodiments are provided so that the disclosure will fully convey the scope of the invention to those skilled in the art. Like numbers refer to like components throughout. The dimensions and thicknesses for some components and layers may be exaggerated for clarity.

Figure 1:
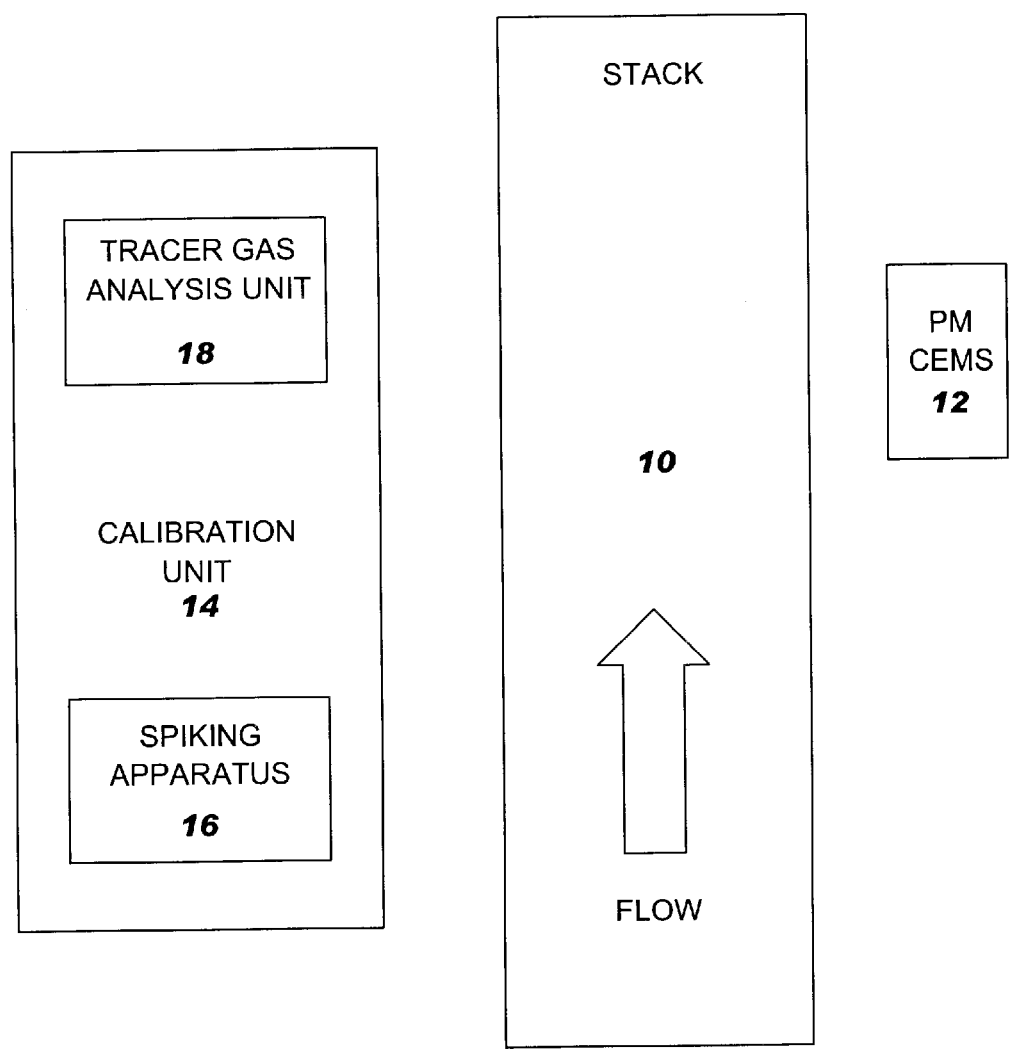
FIG. 1 is a schematic diagram of a flue stack, PM CEMS system, and calibration system of the present invention.

Referring now to FIG. 1, a flue gas stack 10 is illustrated therein. As used herein, the term "stack" refers to any pipe, duct, or exhaust vent that carries gases containing particulate matter. The stack 10 may be associated with any number of different types of industrial apparatus, including industrial furnaces, incinerators, reaction vessels, boilers, smelters, and the like, that produce flue gas as a by-product of a reaction or process that occurs within the apparatus.

The flue gas stack 10 has connected thereto a PM CEMS 12 for monitoring particles traveling out of the stack 10 as part of the flue gas stream. As discussed above, a typical PM CEMS includes an optical device mounted on the stack or a device that extracts and analyzes sample gas to determine the concentration of particulate matter. The PM CEMS may also include a stack flow rate monitoring device to allow for calculation of particulate emissions in units of mass per unit time (e.g. pounds per hour). Those skilled in this art will understand that the PM CEMS 12 can be any of a number of such units available for continuously monitoring the particulate matter exiting a flue gas stack.

Still referring to FIG. 1, a PM CEMS calibration unit 14 is in fluid communication with the PM CEMS 12. The calibration unit 14 includes a particulate spiking apparatus 16 and a tracer gas analysis unit 18, each of which are in fluid communication with the flue gas stack 10. As indicated in FIG. 1, the particulate spiking apparatus 16 is connected to the stack 10 upstream of the PM CEMS 12 and the tracer gas analysis unit 18 is located as close as possible to the PM CEMS 12. The calibration unit 14 is described in greater detail below.

Figure 2:
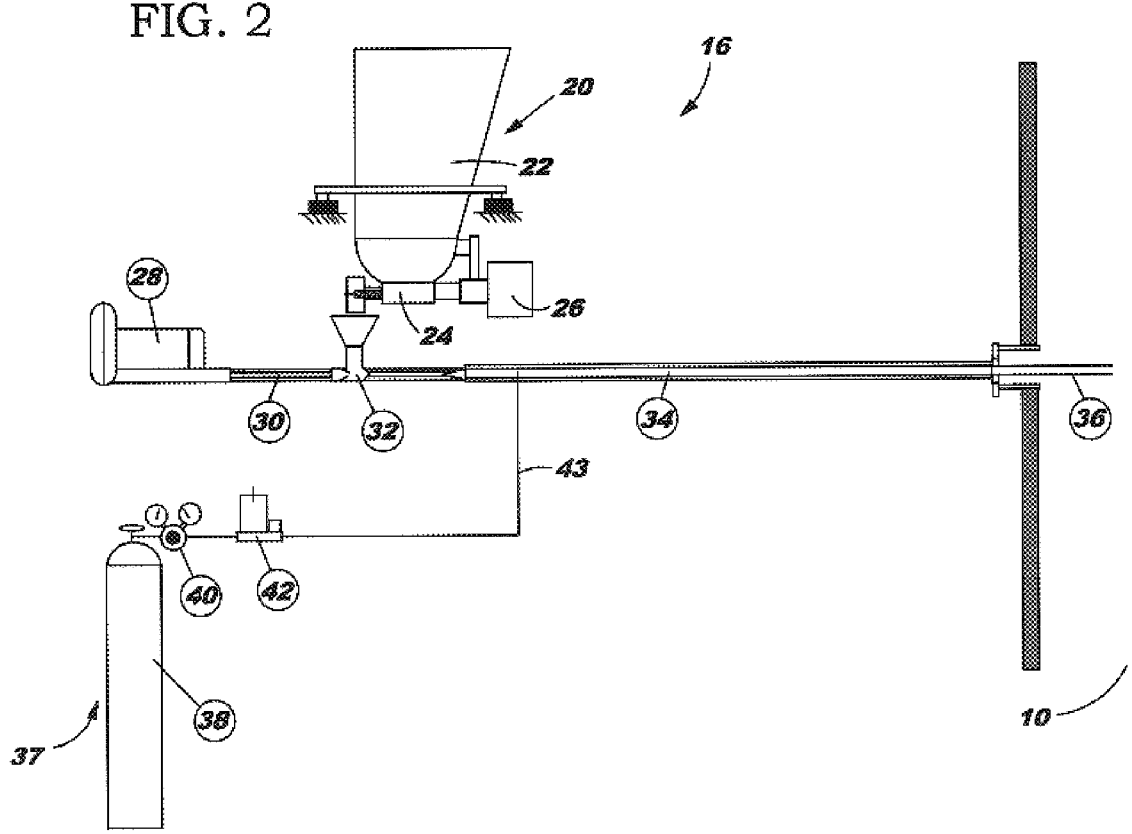
FIG. 2 is a schematic diagram of the major components of the particulate spiking system of the calibration system illustrated in FIG. 1.

Referring now to FIG. 2, the spiking apparatus 16 includes a loss-in-weight solids feeder 20, an air compressor 28, a solids eductor 32, a probe 36, and a tracer gas injection unit 37. These components are interconnected via an eductor inlet 30, an eductor outlet 34, and a tracer gas line 43, which carry gases and particulate matter through the components and into the flue gas stack 10.

Referring still to FIG. 2, the loss-in-weight feeder 20 is configured to store particulate matter and deliver it at a constant mass flow rate to the eductor 32. The particulate matter contained in the feeder 20 should be the same as the typical mix of particulate matter that exits the flue gas stack 10. This can be accomplished by compiling samples from the particulate matter air pollution control device for a given facility.

The feeder 20 includes a feed hopper 22, which should be sized to store a sufficient quantity of particulate matter so that operation of the spiking apparatus 16 need not be interrupted to refill the hopper 22. Also, it is preferred that the feed hopper 22 be configured so that the particulate matter contained therein is not segregated by particle size while residing in the hopper 22. Typically, this can be accomplished by the inclusion of an agitator and steep sides on the hopper 22.

The feeder 20 also includes a screw feeder 24, which receives particulate material from the hopper 22 and provides it to the eductor 32. As illustrated herein, the screw feeder 24 is an augering device that is able to provide particulate material at a uniform flow rate. The auger is sized and the speed is selected appropriately for the desired mass flow rate. The rotational speed of the screw feeder 24 is controlled by a screw speed control unit 26, which monitors the current weight of material in the hopper 22 and continuously adjusts the speed of the screw feeder 24 to maintain the desired mass flow to the eductor 32 on a constant basis.

Those skilled in this art will recognize that, although the illustrated feeder 20 is preferred, numerous devices for providing particulate material at a desired flow rate (such as a constant rotational speed auger or a star valve) are available and may be suitable for use with the present invention. A particularly suitable feeder is the K-TRON Model K2ML-T20 Loss-in-Weight Feeder with K-TRON Smart Conrol Module, available from K-Tron America, Pitman, N.J.

The eductor 32 receives particulate matter from the feeder 20 (in the illustrated embodiment, the eductor 32 receives a selected amount of particulate matter from the screw feeder 24) and fluidizes it into a stream of compressed air or other gas. The eductor 32 is sized according to the desired mass flow rate to ensure that the particulate matter remains fluidized until it enters the flue gas stack 10. Preferably, the eductor 32 is sized such that the air or other gas introduced thereto does not dilute the stream in the stack 10 by more than 10 percent of its volume. A preferred eductor is a 1½ inch solids eductor available from Fox Valve Development Corp., Dover, N.J.

The compressor 28 provides the eductor 32 with a source of compressed air (or other gas, as desired) that can fluidize the particulate matter provided by the feeder 20. The compressor 28 is of conventional construction and should be configured such that it supplies gas at a sufficient pressure and flow rate for the particulate matter to be fluidized in the eductor 32. Typical pressures for the compressor 28 are between about 10 and 15 psi, and typical flow rates are between about 40 and 50 ft$^3$/min. An exemplary compressor 28 is a 50 ft$^3$/min ROTRON blower available from Fox Valve Development Corp., Dover, N.J. Alternatively, a fluidizing unit may comprise other devices capable of delivering the particulate matter to the stack 10, such as an air blower located at either the inlet or outlet of the eductor 32.

The compressor 28 is fluidly connected with the eductor 32 via the eductor inlet line 30. Preferably, the eductor inlet line 30 is heat-traced with an electrical resistance heater or other heat source that enables the air provided by the compressor 28 to remain at a temperature above the dew point (typically between about 30 and 60° C., but this temperature is dependent on the moisture content of the air or gas and the delivery pressure) during its residence time in the eductor 32. The heat source may include a controller (not shown) to continuously adjust the amount of heat provided by the inlet line 30. In some embodiments, it may be preferred to include an air inlet pressure monitor to assess the inlet pressure. A suitable assembly for the inlet line 30 is a 1½ inch diameter stainless steel tube in an electrically heat-traced, insulated bundle that is connected with a thermocouple and temperature controller.

Once the particulate matter from the feeder 20 has been fluidized in the eductor 32 with gas from the compressor 28, the fluidized stream travels from the eductor 32 to the eductor outlet line 34. The eductor outlet line 34 may also be equipped with a heat source (such as an electrical resistance heater or the like) to enable the fluidized particulate matter to reach and maintain a temperature that is appropriate for injection into the stack 10. The desired temperature, which is typically between about 120 and 200° C., depends on the moisture content and temperature of the gas stream in the stack or duct. Preferably, this temperature is maintained as close as possible to the gas temperature in the stack 10; at a minimum, the temperature of the air/particulate mixture should be high enough to prevent appreciable condensation of moisture in the stack 10 at or near the point where the spiked stream is introduced, as such condensation may cause agglomeration of particulate matter and affect the particle size distribution. An exemplary eductor outlet line 34 is a tube like that described for the inlet line 30, but with a smooth bore 1½ inch TEFLON® hose covered with stainless steel braid replacing the stainless steel tube.

Referring still to FIG. 2, the tracer gas injection unit 37 is fluidly connected with the eductor outlet line 34 downstream of the eductor 32. The tracer gas injection unit 37 includes a tracer gas cylinder 38 that provides a tracer gas, such as sulfur hexafluoride or some other gas that is non-reactive with the gases and particulate matter in the stack and easily detectable, to the eductor outlet line 34 through the tracer gas line 43. The tracer gas provides a control to the calibration unit 14 that enables the level of spiked particulate matter to be determined indirectly.

A regulator 40 is positioned on the tracer gas line 43 to control the pressure level of the tracer gas (as an example, a two stage hexafluoride gas regulator with a purge attachment may be used), and a flow meter 42 (such as a mass flowmeter, mass flow controller, or rotameter) is positioned on the tracer gas line 43 downstream of the regulator 42 to measure and control the flow rate of the tracer gas. An exemplary flow meter is a Model 830M mass flow controller, available from Sierra Instruments, Monterey, Calif.

The tracer gas is mixed with the fluidized particulate matter in the eductor outlet line 34. The probe 36 is attached at the downstream end of the eductor outlet line 34 and extends into the interior of the stack 10. Preferably, the probe 36 is located just downstream of any particulate matter control devices (such as baghouses or electrostatic precipitators) and well upstream of the PM CEMS 12. Particularly if there are no flow disturbances to distribute the spiked stream prior to the PM CEMS, it may be preferable to include a dispersion nozzle at the free end of the probe 36. An exemplary probe 36 that is suitable for use with the calibration unit 14 can be formed of a 1½ inch diameter stainless steel tube.

Figure 3:
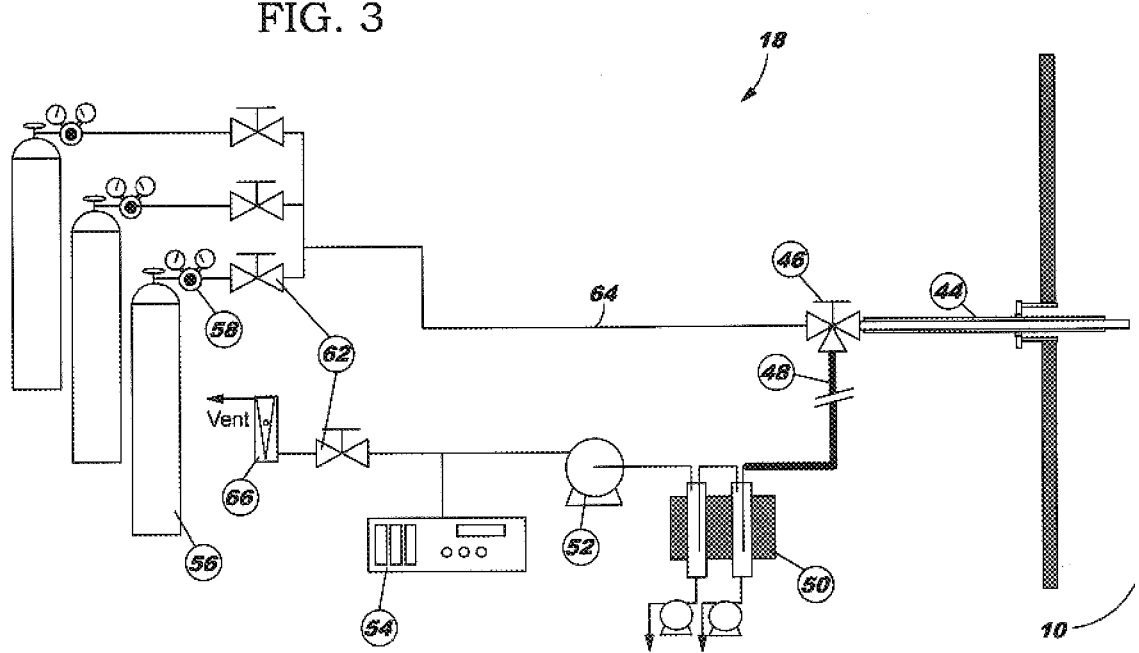
FIG. 3 is a diagram of the flue gas sampling and analysis system of the calibration system illustrated in FIG. 1.

Referring now to FIG. 3, the tracer gas analysis unit 18 includes a receiving probe 44, one or more tracer gas cylinders 56, a three-way calibration gas injection valve 46, a condenser 50, a pump 52, and a tracer gas analyzer 54. These components, which are interconnected via a sample line 48 and a tracer gas line 64, are described in more detail below.

The receiving probe 44 extends into the stack 10 and receives samples of flue gas within its tip. Each sample then travels the length of the receiving probe 44 and into the remainder of the tracer gas analysis unit 18. The receiving probe 44 should be configured to allow the tip to be moved easily within the stack 10 in order to sample individual locations within the stack 10. Typically, the receiving probe 44 is between ¼ and ⅜ inch in diameter; an exemplary receiving probe 44 is a ¼ inch stainless steel tube.

The calibration gas injection valve 46 connects the receiving probe 44, the tracer gas line 64, and the sample line 48. The valve 46 is a three-way valve and enables calibration gas(es) to be injected into the sample received by the receiving probe 44. Preferably, the valve 46 is formed of stainless steel with TEFLON® seats.

Calibration gases are supplied by the cylinders 56, which should contain the same gas as the tracer gas cylinder 38 of the particulate matter spiking apparatus 16 (for example, sulfur hexafluoride). The concentration of tracer gas in the cylinder 56 may vary depending on the exhaust flow rate of the stack 10. Preferably, the concentration of tracer gas in the cylinder 56 is certified by a third party in order to validate testing results.

A regulator 58 is included on the tracer gas line 64 to reduce the pressure at which the tracer gas is provided (an exemplary regulator is a two stage sulfur hexafluoride regulator as set forth above). Also, a flow control valve 62 is located on the tracer gas line 64 to control the pressure and flow rate of the tracer gas into the tracer gas injection valve 46 (a standard ¼ inch stainless steel needle valve can be used).

The sample line 48 leads downstream from the valve 46. The sample line 48 carries a mixture of sample and a known concentration of tracer gas supplied by the tracer gas cylinder 56. Preferably, the sample line 48, which preferably is a ¼ inch TEFLON tube, is heated (for example, by heat tracing) to prevent condensation, which can interfere with maintaining a constant flow rate.

The condenser 50 is connected to the sample line 48 downstream of the valve 46. The condenser 50 receives the sample and cools it below ambient temperature to enable moisture to be removed. An exemplary condenser 50 is a Model ECC-2G gas cooler with a dual head MASTERFLEX peristaltic pump (30 rpm), available from M&C Products, Moorpark, Calif.

From the condenser 50, the sample then travels through the pump 52 (such as a vacuum pump) to the tracer gas analyzer 54, where the concentration of tracer gas is analyzed. The tracer gas analyzer 54 should be configured to detect the concentration of the tracer gas within the sample and provide an output signal that is representative of that concentration. Those skilled in this art will recognize that numerous types of analyzers can carry out this task, including gas chromatographs, Fourier Transform Infrared (FTIR) analyzers and nondispersive infrared (NDIR) analyzers. An exemplary tracer gas analyzer is a Model 101 Fluorotracer gas chromatograph with electron capture detector, available from Conco Systems, Verona, Pa. The tracer gas analyzer 54 may have a flow meter 66 associated with it to monitor gas flow to the analyzer (i.e., to determine whether the analyzer has adequate gas flow and the flow remains constant).

Figure 4:
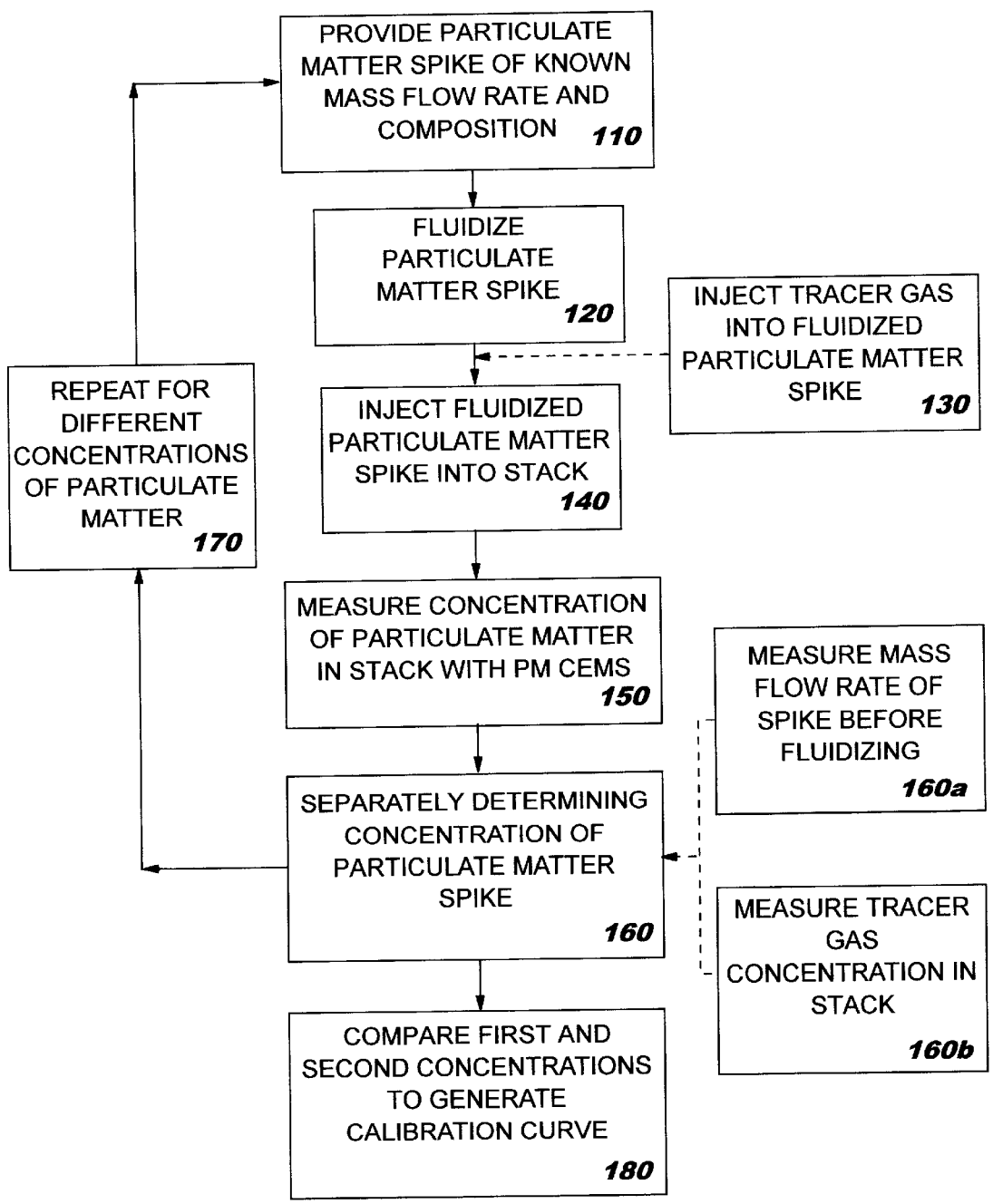
FIG. 4 is a flow chart illustrating a method of calibrating a PM CEMS system according to the present invention.

Operation of the calibration system 14 can be carried out by the process illustrated in FIG. 4. Initially, a representative sample of particulate matter, such as ash or dust, is obtained for the calibration (Box 110). For facilities using fabric filters for particulate matter control, samples obtained equally from the hopper on each compartment or from a central, well-mixed combined mass of particulate matter may be appropriate. For particulate matter control equipment that may segregate collected ash according to particle size (for example, a two-stage electrostatic precipitator), samples should be collected from each hopper proportional to the mass of material collected. The use of method ASTM C311 or an equivalent procedure can provide representative sampling. Alternatively, a representative sample of particulate matter with a similar PM CEMS response may be obtained and used.

Prior to introducing the particulate matter sample into the calibration system, the operator should determine that the PM CEMS 12 to be calibrated has been thoroughly inspected and is in good working order. This should minimize and stabilize the background concentration and make the calibration curve more consistent over time. Alternatively, a test can be conducted during an operating condition where the stack temperature and stack gas composition is similar to normal operation, but without the presence of particulate matter. For incinerators, this can be accomplished by firing natural gas-only without waste feed.

Also, prior to the actual calibration test, a short-term test spike (for example, a spike of having a duration of 30 seconds) should be introduced into the stack 10 to determine the time lag between the initiation of spike input and PM CEMS output. This procedure can enable the operator, during the calibration, to determine at what point the spiking material has reached the PM CEMS 12. It also is preferable to obtain a continuous (at least one sample/second or the minimum frequency available) trend graph of the PM CEMS output signal prior to calibration. Because testing should be avoided during periods when the PM CEMS reading is highly variable, the trend graphs can help to identify prime testing periods.

If a tracer gas is employed during calibration, it may also be preferred to conduct a sampling traverse near the PM CEMS to determine tracer gas concentrations across the duct or stack cross-section. The locations of the traverse points should be selected so that each point represents an equal cross-sectional area of the stack or duct. This may be accomplished using the criteria in EPA Method 5 (40CFR60, Part 60, Appendix A). A relatively constant concentration profile across these traverse points should indicate good mixing of the spiked tracer gas. Determination of the tracer gas concentration at each traverse point can be accomplished using a sample probe, heated sample line, sample conditioner, and gas analyzer as shown in FIG. 3. The gas sampling and analysis method used should ensure accuracy, linearity, and representative nature of the result. The procedures in EPA Method 6C (40CFR60, Appendix A) can obtain accurate sampling and analysis, although the procedures described therein may need to be modified based on the recommendations of the tracer gas analyzer supplier.

Once the stack 10, PM CEMS 12, and calibration system 14 have been prepared, the particulate matter can be introduced into the calibration system 14; in the embodiment illustrated in FIGS. 1 through 3, the particulate matter is introduced into the feeder 20, where it resides in the hopper 22 until it is dispensed by the screw feeder 24. Typically, the concentration of the particulate matter spike will be between about 0.005 and 0.020 grains/dry ft$^3$, and the spike will last for about 90 seconds (preferably at least three times as long as the lag time measured above). If the spike is also being correlated with manual particulate sampling methods, each run may last between 1 and 2 hours. For the first data point, the mass flow rate should be set so as to produce a reading on the PM CEMS that is about 1.5 times the baseline value. Other mass flow rates of particulate matter are determined after the measurement of the first spike, as is discussed below.

The particulate matter spike is fluidized with air or other gas from the compressor 28 in the eductor 32 (Block 120). Typically, air is introduced at a flow rate of between about 40 and 50 ft$^3$/min, and should not exceed 10% of the total stack flow rate.

As discussed above, the use of tracer gas in the calibration system is optional. If tracer gas is to be used, it is introduced into the spiking apparatus 16 downstream of the eductor 32 (Block 130). The tracer gas is injected into the probe 36 at a known flow rate (typically 2 to 3 ft$^3$/min) to mix with the fluidized particulate matter spike.

The tracer gas/fluidized particulate matter mixture is injected into the stack 10 through the probe 36 (Block 140). Preferably, the mixture of tracer gas and fluidized particulate matter is injected near the center of the stack 10. The fluidized mixture should be injected at a flow rate of between about 50 and 60 ft$^3$/min.

Background particulate matter concentration readings from the PM CEMS 12 should be obtained before and after each spike. Data for each spike is preferably taken after spiked gas has been flowing for a period of at least three times the time lag measured above.

Once the particulate matter (either the fluidized particulate matter alone or mixed with tracer gas) has been injected into the stack, the concentration of particulate matter in the stack 10 ($C_s$) is measured with the PM CEMS (Block 150).

Separately, the concentration of particulate matter is determined through another technique to provide comparative data through which a calibration curve can be generated (Block 160). This can be done in at least two different ways depending on whether tracer gas is introduced. In the first method (Sub-block 160a), in which tracer gas is either not employed or not used in the calculation, for each spike period the stack flow rate data from the PM CEMS 12 is obtained in order to calculate a concentration result from the mass flow rate of the spike:

$$C_S = M \times Q_S$$

Where: $C_S$ = concentration of the spike (lb/ft$^3$)

$M$ = mass flow of particulate spike (lb/hr)

$Q_S$ = stack flow (ft$^3$/hr).

The stack flow rate $Q_s$ is measured at the PM CEMS 12, and the mass flow of spiked material M is known from the metering performed at the feeder 20. These values of $C_s$ measured at the PM CEMS 12 and calculated as set forth above can be compared and used to create a calibration curve as described below.

In a second method of determining the concentration of particulate matter in the stack 10, in which tracer gas is employed, the stack flow rate is calculated from the tracer gas flow rate and the measured tracer gas concentration in the stack or duct (Sub-block 160b):

$$Q_S = Q_T(C_T/C_S)$$

Where: $Q_T$ = Flow rate of tracer gas (ft$^3$/min)

$C_T$ = Concentration of tracer gas in cylinder (ppm)

$C_S$ = Concentration of tracer gas in stack or duct (ppm)

Because the concentration of the particulate matter spike within the tracer gas prior to injection is known, the concentration of the spiked particulate matter $C_s$ can be determined from the measured tracer gas concentration $C_s$.

Alternative methods of obtaining stack flow rate data include those described in 40CFR60, Appendix A, Methods 2 and 5.

Once the first data point for particulate matter concentration has been obtained by either of the above methods, this information can be used to approximate the slope (M) of a calibration curve:

$$M = (R_1 - R_0)/C_S$$

Where: $R_1$ = PM CEMS reading during spike $R_0$ = Average of PM CEMS background readings before and after the spike.

The approximate calibration curve is plotted on Cartesian coordinates, with $C_s$ as the "x"-axis and R (the PM CEMS reading) on the "y"-axis. This approximate calibration curve can be used to determine spike rates for subsequent data points. Decisions about the subsequent mass flow rates should be made based on where the points are relative to the regulatory emission rate.

Once the approximate calibration curve is created, additional readings can be taken (i.e., the preceding steps are repeated (Block 170)). These subsequent readings can then be used to create additional data points and generate a refined calibration curve (Block 180). Least square and/or other curve fitting techniques can be used for refining the calibration curve based on subsequent spike runs. If desired, manual particulate test methods (e.g. 40CFR60, Appendix A, Method 5) can be conducted simultaneously with spiking operations to produce measured concentration results for development of calibration curves.

The foregoing embodiments are illustrative of the present invention, and are not to be construed as limiting thereof. The invention is defined by the following claims, with equivalents of the claims to be included therein.

That which is claimed is:

1. An apparatus for calibrating a particulate matter continuous emission monitoring system, said apparatus comprising:
   a feed unit that supplies particulate matter of a known concentration;
   an eductor unit connected with said feed unit that receives particulate matter therefrom;
   a fluidizing unit connected to said eductor that supplies gas to said eductor unit, wherein said particulate matter and gas are combined into a fluidized mixture;
   a probe connected to said eductor configured to extend within an industrial stack and deliver the fluidized mixture therein; and
   an outlet line connecting said eductor unit and said probe, said outlet line including a heat source that heats the outlet line to temperature sufficient to prevent agglomeration of particulate matter.

2. The apparatus defined in claim 1, further comprising a tracer gas injection unit connected with said probe, said tracer gas injection unit configured to inject a tracer gas into said probe to combine with said fluidized mixture.

3. The apparatus defined in claim 2, further comprising a tracer gas analysis unit operatively associated with said stack, said tracer gas analysis unit configured to receive a sample of flue gas from the stack and determine the concentration of tracer gas in said sample.

4. The apparatus defined in claim 3, wherein said tracer gas analysis unit comprises a condenser that removes moisture from said flue gas prior to determination of tracer gas concentration in the sample.

5. The apparatus defined in claim 3, wherein said tracer gas analysis unit further comprises a tracer gas source that supplies tracer gas of a known concentration to said sample.

6. The apparatus defined in claim 1, wherein said feed unit further comprises a feed control unit that monitors the rate at which the feed unit supplies particulate matter to the eductor unit.

7. The apparatus defined in claim 1, further comprising an inlet line connecting said fluidizing unit and said eductor, said inlet line including a heat source that heats gas supplied to said eductor.

8. A method of calibrating a particulate matter continuous emission monitoring system, said method comprising the steps of:
   (a) providing particulate matter of a known composition and mass flow rate;
   (b) fluidizing the particulate matter with a gas;
   (c) injecting the fluidized particulate matter into an industrial stack;
   (d) measuring a first concentration of particulate matter present in the stack with the particulate matter continuous emission monitoring system;
   (e) separately determining a second concentration of particulate matter in the stack;
   (f) repeating steps (a)–(e) for differing concentrations of particulate matter; and
   (g) comparing the first concentrations to the second concentrations to generate a calibration curve for the particulate matter continuous emission monitoring system.

9. The method defined in claim 8, further comprising the step of introducing a tracer gas of known concentration into the fluidized particulate matter prior to step (c), and wherein step (e) comprises:
   drawing a sample of flue gas from the industrial stack; and
   measuring the concentration of the tracer gas in the sample to determine the second concentration of particulate matter.

10. The method defined in claim 9, wherein said tracer gas is sulfur hexafluoride.

11. The method defined in claim 9, further comprising the step of reducing the temperature of the sample prior to said measuring step.

12. The method defined in claim 9, further comprising the step of introducing a known concentration of tracer gas to the sample prior to said measuring step.

13. The method defined in claim 8, further comprising the step of projecting a calibration curve based on the results of steps (d) and (e), and wherein step (f) comprises repeating steps (a) through (e) with concentrations determined based on said projection step.

14. The method defined in claim 8, wherein step (e) comprises measuring the concentration of the particulate matter prior to step (b).

15. The method defined in claim 8, further comprising the step of heating the fluidized mixture prior to step (c).

16. The method defined in claim 8, further comprising the steps of:
   determining a baseline concentration of particulate matter prior to step (b), and
   selecting the known concentration of particulate matter based on the results of the step of determining the baseline concentration.

17. The method defined in claim 8, further comprising the steps of:
   measuring the duration required for particulate matter to travel from an injection location and the particulate matter continuous emission monitoring system; and
   selecting a duration for step (c) that is at least three times as long as the duration measured in said duration measuring step.

18. An apparatus for calibrating a particulate matter continuous emission monitoring system, said apparatus comprising:
   a feed unit that supplies particulate matter of a known concentration;
   an eductor unit connected with said feed unit that receives particulate matter therefrom;
   a fluidizing unit connected to said eductor that supplies gas to said eductor unit, wherein said particulate matter and gas are combined into a fluidized mixture;
   a probe connected to said eductor configured to extend within an industrial stack and deliver the fluidized mixture therein; and
   a tracer gas injection unit connected with said probe, said tracer gas injection unit configured to inject a tracer gas into said probe to combine with said fluidized mixture.

19. The apparatus defined in claim 18, further comprising a tracer gas analysis unit operatively associated with said stack, said tracer gas analysis unit configured to receive a sample of flue gas from the stack and determine the concentration of tracer gas in said sample.

20. The apparatus defined in claim 19, wherein said tracer gas analysis unit comprises a condenser that removes moisture from said flue gas prior to determination of tracer gas concentration in the sample.

21. The apparatus defined in claim 19, wherein said tracer gas analysis unit further comprises a tracer gas source that supplies tracer gas of a known concentration to said sample.

22. The apparatus defined in claim 18, wherein said feed unit further comprises a feed control unit that monitors the rate at which the feed unit supplies particulate matter to the eductor unit.

23. The apparatus defined in claim 18, further comprising an inlet line connecting said fluidizing unit and said eductor, said inlet line including a heat source that heats gas supplied to said eductor.

24. An apparatus for calibrating a particulate matter continuous emission monitoring system, said apparatus comprising:
 a feed unit that supplies particulate matter of a known concentration;
 an eductor unit connected with said feed unit that receives particulate matter therefrom;
 a fluidizing unit connected to said eductor that supplies gas to said eductor unit, wherein said particulate matter and gas are combined into a fluidized mixture;
 a probe connected to said eductor configured to extend within an industrial stack and deliver the fluidized mixture therein; and
 an inlet line connecting said fluidizing unit and said eductor, said inlet line including a heat source that heats gas supplied to said eductor.

25. The apparatus defined in claim 24, further comprising a tracer gas injection unit connected with said probe, said tracer gas injection unit configured to inject a tracer gas into said probe to combine with said fluidized mixture.

26. The apparatus defined in claim 25, further comprising a tracer gas analysis unit operatively associated with said stack, said tracer gas analysis unit configured to receive a sample of flue gas from the stack and determine the concentration of tracer gas in said sample.

27. The apparatus defined in claim 26, wherein said tracer gas analysis unit comprises a condenser that removes moisture from said flue gas prior to determination of tracer gas concentration in the sample.

28. The apparatus defined in claim 26, wherein said tracer gas analysis unit further comprises a tracer gas source that supplies tracer gas of a known concentration to said sample.

29. The apparatus defined in claim 24, wherein said feed unit further comprises a feed control unit that monitors the rate at which the feed unit supplies particulate matter to the eductor unit.

* * * * *